United States Patent
Goldstein et al.

(10) Patent No.: US 7,285,561 B2
(45) Date of Patent: Oct. 23, 2007

(54) IMIDAZO-SUBSTITUTED COMPOUNDS AS P38 KINASE INHIBITORS

(75) Inventors: David Michael Goldstein, San Jose, CA (US); Ronald Charles Hawley, Mountain View, CA (US); Alfred Sui-Ting Lui, Redwood City, CA (US); Eric Brian Sjogren, Mountain View, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 11/486,348

(22) Filed: Jul. 13, 2006

(65) Prior Publication Data

US 2006/0252784 A1 Nov. 9, 2006

(51) Int. Cl.
C07D 471/04 (2006.01)
A61K 31/4184 (2006.01)
A61K 31/4188 (2006.01)
A61P 19/02 (2006.01)
A61P 25/28 (2006.01)
A61P 11/00 (2006.01)
C07D 487/04 (2006.01)
A61K 31/519 (2006.01)

(52) U.S. Cl. .................. 514/293; 546/82; 544/251; 514/267

(58) Field of Classification Search ............... 546/82; 514/294, 293
See application file for complete search history.

(56) References Cited

U.S. PATENT DOCUMENTS 4,522,947 A 6/1985 Musser et al.
4,650,737 A 3/1987 Wiedemann
4,656,281 A 4/1987 Musser et al.
4,831,040 A 5/1989 Decktor et al.

FOREIGN PATENT DOCUMENTS

EP 0542497 A1 5/1993
JP 11-292878 A2 4/1998
WO WO 02/064594 A2 8/2002

OTHER PUBLICATIONS

Wolft Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
Cecil Textbook of Medicine, edited by Bennet, J.C., and Plum F., 20th edition,vol. 1, 1004-1010, 1996.*
See Graninger et al. Curr. Opin. Rheumatol. 13(3): 209-213.*
Nagarkatti et al. J. Mol. Cell Cardiol. 30(8): 1651-1664, 1998.*
Brunet et al., Esaays Biochem. 32 : 1-16, 1997.*
Herlaar et al. Mol. Med. Today 5(10) 439-447,1999.*

* cited by examiner

*Primary Examiner*—Venkataraman Balasubramanian
(74) *Attorney, Agent, or Firm*—Grant D. Green

(57) ABSTRACT

The present invention discloses compounds corresponding to formula I:

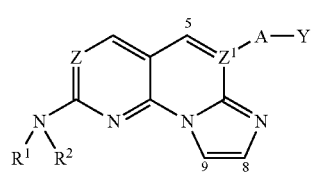

wherein A, Z, $Z^1$, Y, $R^1$ and $R^2$ are as defined in the specification, as well as pharmaceutical formulations, methods of making and uses thereof.

10 Claims, No Drawings

IMIDAZO-SUBSTITUTED COMPOUNDS AS P38 KINASE INHIBITORS

RELATED APPLICATIONS

This application claims the benefit of U.S. Ser. No. 11/122,137, filed May 4, 2005, now U.S. Pat. No. 7,081,462, which is a division of U.S. Ser. No. 10/406,364, filed Apr. 3, 2003, now U.S. Pat. No. 6,949,560, which in turn is based on U.S. Provisional Application Ser. No. 60/369,929, filed Apr. 3, 2002, pursuant to 35 U.S.C. § 119(e) the contents of which are incorporated herein by reference in full.

FIELD OF THE INVENTION

The present invention relates to certain heterocylic compounds as p38 protein kinase inhibitors. In particular, the present invention relates to imidazo-substituted hetero-bicyclic compounds, a process for their manufacture, pharmaceutical preparations comprising the same, and methods for using the same.

BACKGROUND OF THE INVENTION

Mitogen-activated protein kinases (MAP) is a family of proline-directed serine/threonine kinases that activate their substrates by dual phosphorylation. The kinases are activated by a variety of signals including nutritional and osmotic stress, UV light, growth factors, endotoxin and inflammatory cytokines. One group of MAP kinases is the p38 kinase group which includes various isoforms (e.g., p38α, p38β, p38δ and p38γ). The p38 kinases are responsible for phosphorylating and activating transcription factors as well as other kinases, and are themselves activated by physical and chemical stress, pro-inflammatory cytokines and bacterial lipopolysaccharide.

More importantly, the products of the p38 phosphorylation have been shown to mediate the production of inflammatory cytokines, including TNF, IL-1, IL-6 and cyclooxygenase-2. Each of these cytokines has been implicated in numerous disease states and conditions. For example, TNF-α is a cytokine produced primarily by activated monocytes and macrophages. Its excessive or unregulated production has been implicated as playing a causative role in the pathogenesis of rheumatoid arthritis. More recently, inhibition of TNF production has been shown to have broad application in the treatment of inflammation, inflammatory bowel disease, Alzheimer's disease, Crohn's disease, multiple sclerosis and asthma.

TNF has also been implicated in viral infections, such as HIV, influenza virus, and herpes virus including herpes simplex virus type-1 (HSV-1), herpes simplex virus type-2 (HSV-2), cytomegalovirus (CMV), varicella-zoster virus (VZV), Epstein-Barr virus, human herpes virus-6 (HHV-6), human herpes virus-7 (HHV-7), human herpes virus-8 (HHV-8), pseudorabies and rhinotracheitis, among others.

Similarly, IL-1 is produced by activated monocytes and macrophages, and plays a role in many pathophysiological responses including rheumatoid arthritis, fever and reduction of bone resorption.

The inhibition of these cytokines by inhibition of the p38 kinase is of benefit in controlling, reducing and alleviating many of these disease states.

SUMMARY OF THE INVENTION

In one aspect, the present invention provides compounds represented by the formula I:

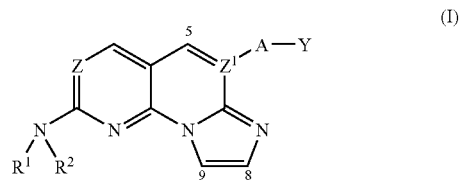

(I)

wherein:
Z is N or CH;
$Z^1$ is selected from N and CH when the bond between atoms C5 and $Z^1$ is a single bond, and $Z^1$ is C when the bond between C5 and $Z^1$ is a double bond;
$R^1$ is hydrogen or alkyl;
$R^2$ is alkyl, aralkyl, cycloalkyl, heteroalkyl, heterocyclyl, aryl, or heteroaryl;
A is absent or —O—, —CHR'—, —C(=O)—, —S(O)$_n$—, or —NR$^{3-}$, wherein n is 0, 1, or 2, R' is hydrogen or alkyl, and $R^3$ is hydrogen, alkyl, aryl, heteroaryl, or cycloalkyl;
the bond between atoms C5 and $Z^1$ is a single or double bond;
the bond between atoms C8 and C9 is a single or double bond; and
Y is an alkyl, heteroalkyl, cycloalkyl, aryl, or heteroaryl; or isomers, pharmaceutically acceptable salts, esters or prodrugs thereof.

The compounds of formula I and their aforementioned salts are inhibitors of protein kinases and exhibit effective activity against p38 in vivo. Therefore, the compounds can be used for the treatment of diseases mediated by the pro-inflammatory cytokines such as TNF and IL-1.

Thus, in another aspect, the present invention relates to methods for the treatment of p38 mediated diseases or conditions in which a therapeutically effective amount of a compound of formula I is administered to a patient in need of such treatment.

In yet another aspect, the present invention relates to methods for preparing the compounds described above.

In yet still another aspect, the present invention relates to methods for preparing medicaments useful for the treatment of the p38 mediated diseases and conditions.

DEFINITIONS

As used herein, the term "alkyl" means a linear saturated monovalent hydrocarbon radical or a branched saturated monovalent hydrocarbon radical of one to six carbon atoms, e.g., methyl, ethyl, n-propyl, 2-propyl, tert-butyl, pentyl, and the like.

The term "aryl" refers to a monovalent monocyclic or bicyclic aromatic hydrocarbon radical which is optionally substituted independently with one or more substituents. When an aryl group is substituted with, preferably one, two or three, substituents, the substituents are preferably selected from the group consisting of alkyl, haloalkyl, halo, hydroxy, nitro, cyano, amino, haloalkoxy, heteroalkyl, methylenedioxy, ethylenedioxy, Y-aryl, Y-heteroaryl, Y-cycloalkyl, Y-heterocyclyl, Y—OR$^p$—Y—NR$^p$R$^q$, —Y—C(O)—R$^p$, —YS(O)$_{0-2}$R$^p$, —Y—N—S(O)$_2$R$^p$, —Y—S(O)$_2$NR$^p$R$_q$, —Y—N—C(O)NR$^p$R$^q$, where Y is absent or a $C_1$-$C_3$ alkylene group, and R$^p$ and R$^q$ are each independently from each other selected from hydrogen, alkyl, haloalkyl, hydroxy, alkoxy, aryl, heteroaryl, cycloalkyl, and heterocyclyl. More specifically the term aryl includes, but is not limited to, phenyl, chlorophenyl, methoxyphenyl, 1-naphthyl, 2-naphthyl, and the derivatives thereof.

"Aralkyl" means a radical —R$^x$R$^y$ where R$^x$ is an alkylene group and R$^y$ is an aryl group as defined above, e.g. benzyl, phenylethylene, and the like.

The term "cycloalkyl" as used herein refers to a saturated monovalent cyclic hydrocarbon radical of three to seven ring carbons, e.g., cyclopentyl, cyclobutyl, cyclohexyl, and the like. The saturated monovalent cyclic hydrocarbon radical as defined above, may be optionally substituted with one, two or three substituents which are not hydrogen. Preferably, the substituents are selected from the group consisting of alkyl, hydroxy, alkoxy, amino, monosubstituted amino, disubstituted amino, haloalkyl, halo, cyanoalkyl, oxo (i.e., carbonyl oxygen), heteroalkyl, heterocyclyl, hydroxyalkyl, and —(X)$_n$—C(O)R' (where, X is O or NR", n is 0 or 1, R" is hydrogen, alkyl, haloalkyl, amino, monosubstituted amino, disubstituted amino, hydroxy, alkoxy, alkyl or optionally substituted phenyl, and R' is H or alkyl), and —S(O)$_n$R' (wherein n is 0 to 2). More specifically, the term substituted cycloalkyl includes, for example, substituted cyclopentyl, substituted cyclohexyl, and the like.

The term "halo," "halide" or "halogen," when referring to a substituent means fluoro, chloro, bromo, or iodo, preferably chloro.

The term "haloalkyl" means alkyl substituted with one or more same or different halo atoms, e.g., —CH$_2$Cl, —CF$_3$, —CH$_2$CF$_3$, —CH$_2$CCl$_3$, and the like, and further includes those alkyl groups such as perfluoroalkyl in which all alkyl hydrogen atoms are replaced by fluorine atoms.

The term "heteroalkyl" as used herein means an alkyl radical defined above, wherein one, two or three hydrogen atoms have been replaced with a substituent independently selected from the group consisting of —OR$^a$, —NR$^b$R$^c$, and S(O)$_n$R$^d$ (where n is an integer from 0 to 2), with the understanding that the point of attachment of the heteroradical is through a carbon atom, wherein R$^a$ is hydrogen, acyl, alkyl, cycloalkyl, or cycloalkylalkyl; or R$^b$ and R$^c$ are independently of each other hydrogen, acyl, alkyl, cycloalkyl, or cycloalkylakyl, or R$^b$ and R$^c$ together with the nitrogen atom to which they are attached form heterocyclo or heteroaryl; and when n is 0, R$^d$ is hydrogen, alkyl, cycloalkyl, or cycloalkylakyl, and when n is 1 or 2, R$^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxymethylethyl, 2,3-dihydroxypropyl, 1-hydroxy-methylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, methylaminosulfonylmethyl, methylaminosulfonylethyl, methylaminosulfonylpropyl, and the like. When R$^a$ is hydrogen, the radical —OR$^a$ is also referred to as "hydroxyalkyl" and includes, but is not limited to, 2-hydroxyethyl, 3-hydroxypropyl, 2-hydroxymethylethyl, 2,3-dihydroxypropyl, 1-hydroxymethylethyl, 3-hydroxybutyl, 2,3-dihydroxybutyl, and 2-hydroxy-1-methylpropyl.

"Heteroaryl" means a monvalent monocyclic or bicyclic radical of 5 to 12 ring atoms having at least one aromatic ring containing one, two, or three ring heteroatoms selected from N, O, or S, the remaining ring atoms being C, with the understanding that when the heteroaryl is a bicyclic system in which one of the rings is carbocyclic and/or non-aromatic, the attachment point of the heteroaryl radical will be on a heteroaryl ring. The heteroaryl ring is optionally substituted with one or more substituents, preferably one or two substituents, independently from each other selected from alkyl, haloalkyl, halo, nitro, cyano, amino, methylenedioxy, Y-aryl, Y-heteroaryl, Y-cycloalkyl, —Y-heterocyclyl, —Y—OR', —YNR'R", —Y—C(O)R', —Y—O—C(O)—R', —Y—S(O)$_{0-2}$—R', —Y—N—SO$_2$—R', —Y—SO$_2$—NR'R", and —Y—N—C(O)—NR'R", where Y is absent or a $C_1$-$C_3$ alkylene group and R' and R" are each independently from each other hydrogen, alkyl, haloalkyl, hydroxy, alkoxy, aryl, heteroaryl, cycloalkyl, or heterocyclyl. More specifically, the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, benzofuranyl, tetrahydrobenzofuranyl, isobenzofuranyl, benzothiazolyl, benzoiosthiazolyl, benzotriazolyl, indolyl, isoindolyl, benzoxazolyl, quinolyl, tetrahydroquinolnyl, isoquinolyl, benzimidazolyl, benzisoxazolyl or benzothienyl, imidazo[1,2-a]-pryidinyl, imidazo[2,1-b]thiazolyl, and derivatives thereof.

"Monosubstituted amino" means a radical —NHR$^e$ where R$^e$ is alkyl, heteroalkyl, haloalkyl, cycloalkyl, cycloalkylalkyl, hydroxyalkyl, aryl, aralkyl, aralkenyl, heteroaryl, heteroaralkyl, heteroaralkenyl, heterocyclyl, or heterocyclylalkyl, e.g., methylamino, ethylamino, phenylamine, benzylamine, and the like. Similarly, the term "disubstituted amino" refers to a radical —NR$^g$R$^h$ wherein R$^g$ and R$^h$ are, independently of each other, alkyl, heteroalkyl, haloalkyl, cycloalkyl, cycloalkylalkyl, hydroxyalkyl, aryl, aralkyl, aralkenyl, heteroaryl, heteroaralkyl, heteroaralkenyl, heterocyclyl, or heterocyclylalkyl, or R$^g$ and R$^h$ together with the nitrogen atom to which they are attached form a heterocyclyl ring. Representative examples include, but are not limited to, dimethylamino, methylethylamino, di(1-methyl-ethyl) amino, piperazinyl, and the like.

"Heterocyclyl" means a saturated cyclic radical in which one or two ring atoms are heteroatoms selected from N, O, or S(O)$_n$ (where n is an integer from 0 to 2), the remaining ring atoms being C, where one or two C atoms may optionally contain a carbonyl oxygen group, e.g., one or two atoms in the ring may be a moiety of the formula —C(=O)—. The heterocyclyl ring may be optionally substituted independently with one, two, or three substituents selected from alkyl, hydroxy, hydroxyalkyl, alkoxy, heteroalkyl, haloalkyl, and —(X)$_n$—C(O)R (where, X is O or NR', n is 0 or 1, R is hydrogen, alkyl, haloalkyl, amino, monosubstituted amino, disubstituted amino, hydroxy, alkoxy, or optionally-substituted phenyl, and R' is H or alkyl), Y-aryl, Y-heteroaryl, Y-cycloalkyl, Y-heterocyclyl, Y—OR$^p$, —Y—NR$^p$R$^q$, —Y—C(O)—R$^p$, —YS(O)$_{0-2}$R$^p$, —Y—N—S(O)$_2$R$^p$, —Y—S(O)$_2$NR$^p$R$^q$, —Y—N—C(O) NR$^p$R$^q$, where Y is absent or a $C_1$-$C_3$ alkylene group, and R$^p$ and R$^q$ are each independently from each other selected from hydrogen, alkyl, haloalkyl, hydroxy, alkoxy, aryl, heteroaryl, cycloalkyl, and heterocyclyl. More specifically the term heterocyclyl includes, but is not limited to, tetrahydropyranyl, piperidinyl, piperazinyl, morpholinyl, and the derivatives thereof.

The term "acyl" refers to the group —C(O)R$^r$ where R$^r$ is alkyl, haloalkyl, heteroalkyl, aryl, heteroaryl, aralkyl or heteroaralkyl.

"Alkoxy", "aryloxy", "aralkyloxy", or "heteroaralkyloxy" means a radical —OR where R is an alkyl, aryl, aralkyl, or heteroaralkyl, respectively, as defined above, e.g., methoxy, phenoxy, pyridin-2-ylmethyloxy, benzyloxy, and the like.

When a bond appears in a formula herein as a double bond wherein one of the two bonds appears as a dotted line, as in

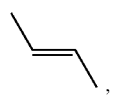

it should be understood that unless otherwise specifically stated, this notation means the bond optionally may be a single bond or a double bond, with appropriate selections being made for adjacent atoms. Thus, when it is stated "the dotted line is a bond," this means a double bond is present; and when it is stated "the dotted line is not a bond," this means a single bond is present.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Pharmaceutically acceptable excipient" means an excipient that is useful in preparing a pharmaceutical composition that is generally safe, non-toxic and neither biologically nor otherwise undesirable, and includes excipients that are acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethamine, N-methylglucamine, and the like.

The terms "pro-drug" and "prodrug" are used interchangeably herein and refer to any compound which releases an active parent drug according to Formula I in vivo when such prodrug is administered to a mammalian subject. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of Formula I, and the like.

"Protecting group" refers to a grouping of atoms that when attached to a reactive group in a molecule masks, reduces or prevents that reactivity. Examples of protecting groups can be found in T. W. Green and P. G. Futs, *Protective Groups in Organic Chemistry*, (Wiley, $2^{nd}$ ed. 1991) and Harrison and Harrison et al., *Compendium of Synthetic Organic Methods*, Vols. 1-8 (John Wiley and Sons, 1971-1996). Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

DETAILED DESCRIPTION OF THE INVENTION

In one embodiment, the present invention provides compounds represented by the formula:

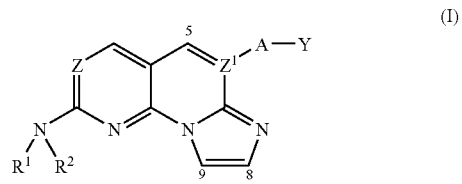

(I)

wherein Z, $Z^1$, $R^1$, $R^2$, A, Y, and the bonds between C5 and $Z^1$ and C8 and C9 are as defined above.

Preferred compounds of formula I includee those wherein A is absent or —O—, both Z and $Z^1$ are N, Y is an aryl, $R^1$ is hydrogen, and $R^2$ is as defined above for compounds of formula (I). More preferred compounds are compounds of formula I, wherein Z is N, $Z^1$ is C such that the bond between C5 and $Z^1$ is a double bond, A is absent or —O, Y is aryl (more preferably optionally-substituted phenyl), $R^1$ is hydrogen, and $R^2$ is as defined above for compounds of formula I.

Still more preferred compounds are compounds of formula I(a):

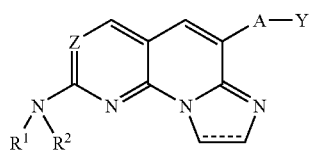

wherein Z is N, A or absent or —O—, Y is optionally-substituted phenyl, $R^1$ is hydrogen, and $R^2$ is as defined above.

Most preferred compounds are those of formula I(a) wherein Z is N, A is absent, Y is a phenyl substituted with a halo, hydroxy, amino, alkyl or heteroalkyl, $R^1$ is hydrogen, and $R^2$ is alkyl, heteroalkyl, optionally-substituted cycloalkyl, optionally-substituted heterocycyl or substituted phenyl or benzyl.

Particularly preferred compounds are compounds of formula I(a) wherein A is absent, Y is phenyl substituted with a halo, the dotted line is a double bond, $R^1$ is hydrogen, and $R^2$ is alkyl (more preferably lower alkyl optionally substituted with hydroxy, methoxy or methylsulfonyl), heteroalkyl, optionally-substituted cycloalkyl (more preferably cyclopentyl or cyclohexyl optionally substituted with methoxy), optionally-substituted heterocycyl (more preferably optionally-substituted piperidinyl), or substituted phenyl or benzyl (more preferably phenyl or benzyl substituted with a halo). Table I below lists some of the representative compounds of formula I(a).

Other representative compounds of the invention are compounds of formula I(b).

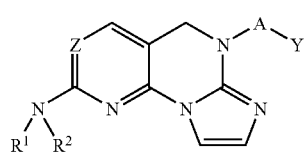

wherein $R^1$, Z, $R^2$, A and Y are as defined above for compounds of formula (I) and I(a).

Still other representative compounds of the invention are compounds of formula I(c)

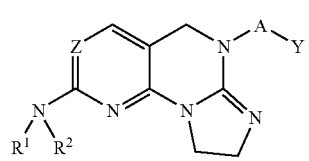

wherein Z, $R^1$, $R^2$, A and Y are as defined above for compounds of formula (I) and I(a).

A preferred compound (12) of formula I(c) is wherein Z is N, A is absent, $R^1$ is hydrogen, Y is 2-chlorophenyl, and $R^2$ is 4-hydroxycyclohexyl. Mass spectra of MH+399.

TABLE 1

Representative compounds of formula I(a) are compounds wherein the dotted line is a bond, Z is N, $R^1$ is hydrogen, and the values of $R^2$, A, and Y are as set forth below:

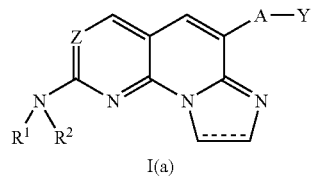

I(a)

| Cpd # | $R^2$ (name) | $R^2$ (structure) | A | Y | Mp °C. | MH+ |
|---|---|---|---|---|---|---|
| 1 | 4-hydroxycyclohexyl | HO—⬡— | absent | 2-chlorophenyl | 116-119 | 394 |
| 2 | tetrahydropyran-4-yl | O⬡— | absent | 2-chlorophenyl | 211-214 | 380 |
| 3 | (N-methylsulfonyl)piperidin-4-yl | H₃C—S(O)(O)—N⬡— | absent | 2-chlorophenyl | 188-194 | 457 |

TABLE 1-continued

Representative compounds of formula I(a) are compounds wherein the dotted line is a bond, Z is N, R¹ is hydrogen, and the values of R², A, and Y are as set forth below:

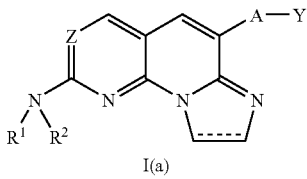

I(a)

| Cpd # | R² (name) | R² (structure) | A | Y | Mp ° C. | MH+ |
|---|---|---|---|---|---|---|
| 4 | Cyclopentyl | | absent | 2-chlorophenyl | 247.5-249 | 364 |
| 5 | 4-tetrahydro-1,1-dioxide-2-H-thiopyranyl | | absent | 2-chlorophenyl | 221.8-226.8 | 428 |
| 6 | 1-(1,1-dimethyl-2-hydroxy)ethyl | | absent | 2-chlorophenyl | 190.8-194.3 | 368 |
| 7 | Isopropyl | | absent | 2-chlorophenyl | 210-212.5 | 338 |
| 8 | 4-fluorobenzyl | | absent | 2-chlorophenyl | 178-180 | 404 |
| 9 | 1-(2-methylsulfonyl)-ethyl | | absent | 2-chlorophenyl | 172.2-176 | 402 |
| 10 | tetrahydropyran-4-yl | | O | 4-fluorophenyl | 169.3-175.8. | 380 |
| 11 | 4-fluorophenyl | | O | 4-fluorophenyl | 198-206 | 390 |

A preferred compound (13) of formula I(a) is a compound wherein Z is N, the dotted line is not a bond, R¹ is hydrogen, R² is 4-hydroxycylcohexyl, and Y is 2-chlorophenyl. MH+ 396, M.P. 169.3° C. to 175.8° C.

Particularly preferred compounds of formula I(a) are compounds (3) and (7) of Table 1, above.

The compounds of the present invention can exist in unsolvated forms as well as solvated forms, including hydrated forms and are intended to be encompassed within the scope of the invention. Furthermore, as stated above, the present invention also includes all pharmaceutically acceptable salts of the compounds along with prodrug forms of the compounds and all stereoisomers whether in a pure chiral form or a racemic mixture of other forms of mixture.

The compounds of formula I are capable of further forming pharmaceutically acceptable acid addition salts. All of these forms are also contemplated within the scope of the claimed invention.

Pharmaceutically acceptable acid addition salts of the compounds of formula I include salts derived from inorganic acids such as hydrochloric, nitric, phosphoric, sulfuric, hydrobromic, hydriodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, pthalate, benzenesulfonate, toluenesulfonate, phenylacetate, citrate, lactate, maleate, tartarate, methanesulfonate, and the like. Also contemplated are salts of amino acids such as arginate and the like and gluconate, galacturonate (see, for example, Berge et al., "Pharmaceutical Salts," *J. of Pharmaceutical Science*, 1977, 66, 1-19).

The acid addition salts of the basic compounds can be prepared by contacting the free base form with a sufficient amount of the desired acid to produce the salt in the conventional manner. The free base form can be regenerated by contacting the salt form with a base and isolating the free base in the conventional manner. The free base forms may differ from their respective salt forms somewhat in certain physical properties such as solubility in polar solvents, but otherwise the salts are equivalent to their respective free base for the purposes of the present invention.

Pharmaceutically acceptable base addition salts can be formed with metal ions or amines, such as alkali and alkaline earth metal ions or organic amines. Examples of metal ions which are used as cations include sodium, potassium, magnesium, calcium, and the like. Examples of suitable amines are N,N'-dibenzylethylenediamine, chlororocaine, choline, diethanolamine, ethylenediamine, N-methylglucamine, and procaine (see, for example, Berge et al., supra).

The basic addition salts of acidic compounds can be prepared by contacting the free acid form with a sufficient amount of the desired base to produce the salt in the conventional manner. The free acid form can be regenerated by contacting the salt form with an acid and isolating the free acid in the conventional manner. The free acid forms may differ from their respective salt forms somewhat in certain physical properties such as solubility in polar solvents, but otherwise the salts are equivalent to their respective free acid for the purposes of the present invention.

All patents, patent applications and publications cited in this application are hereby incorporated by reference in their entirety for all purposes to the same extent as if each individual patent, patent application or publication were so individually denoted.

Processes for Preparing the Compounds

The compounds of the present invention can be prepared by a variety of methods, using procedures well-known to those of skill in the art. The following schemes illustrate the processes of making the compounds of the invention.

Abbreviations

The abbreviations used herein have the following meaning:
MCPBA: m-chloroperbenzoic acid.
NMP: 1-methyl-2-pyrrolidinone.
THF: tetrahydrofuran.
TLC: thin layer chromatography.
EtOAc: ethyl acetate.
LAH: lithium aluminum hydride.
DMF: dimethylformamide
DMPU: 1,3-dimethyl-3,4,5,6-tetrahydro-2(1H)-pyrimidinone Scheme 1

Scheme 1 describes a general method of synthesizing compounds of formula I(a) (1) (compounds of formula I(a) wherein the dotted line is not a bond) starting with a protected thiopyridine-5-carboxylate 1, wherein $R^P$ and $R^{pa}$ are protecting groups such as lower alkyl and benzyl; and $R^L$ is a leaving group such as a halo. The protecting and leaving groups are as defined on page 6, lines 30 through page 7, line 9 and page 5, lines 22-26, respectively. The general method of preparing compound 5 from carboxylate 1 in the Scheme is described in WO 0129042 and WO 0129041.

Compound 1 is treated with triethylamine and aqueous ammonium to afford compound 2. Compound 2 is reduced with lithium aluminum hydride or other reducing agents well known in the art to yield compound 3. Compound 3 is oxidized to aldehyde 4 by treating it with activated manganese oxide powder or by other oxidizing methods known in the art. Compound 4 is reacted with an ester of general formula -A-Y—C(O)$OR^z$, wherein A and Y are as defined above and $R^z$ is lower alkyl, aryl or cycloalkyl, to afford pyrimidinone 5.

Compound 5 is reacted with N-(2-hydroxyethyl)-phthalimide to obtain phthalimide 6. The phthalimide 6 is stirred with hydrazine monohydrate and compound 7 isolated in a pure form. Compound 7 is cyclized into tricyclic sulfide 8 by reacting it with trimethylaluminum.

Tricyclic sulfide 8 may be directly reacted with an amine of the general formula —$NH_2R^1R^2$ to afford a compound of general formula I(a)(1).

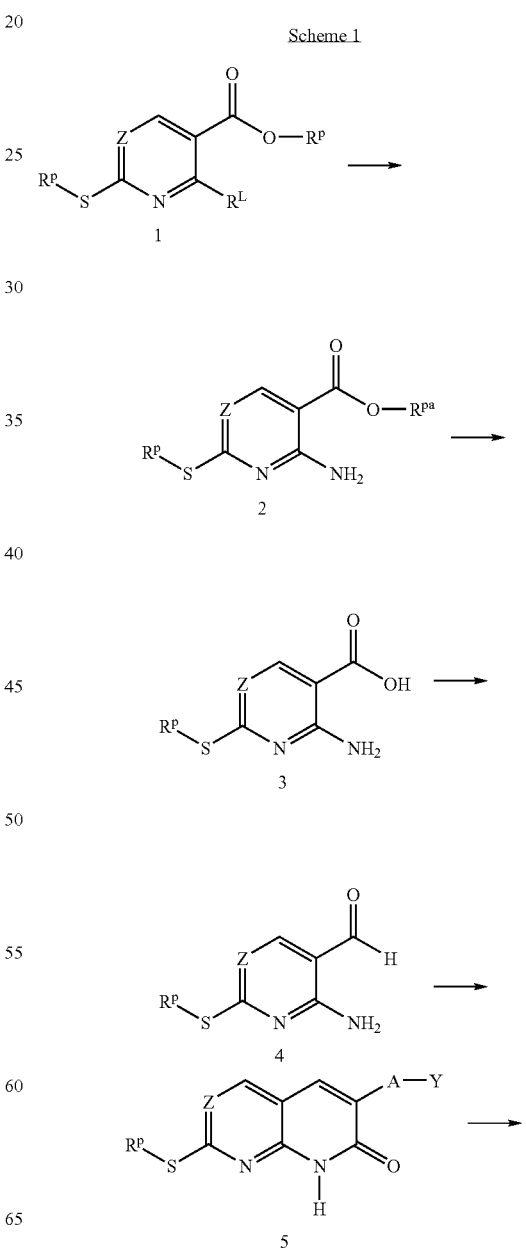

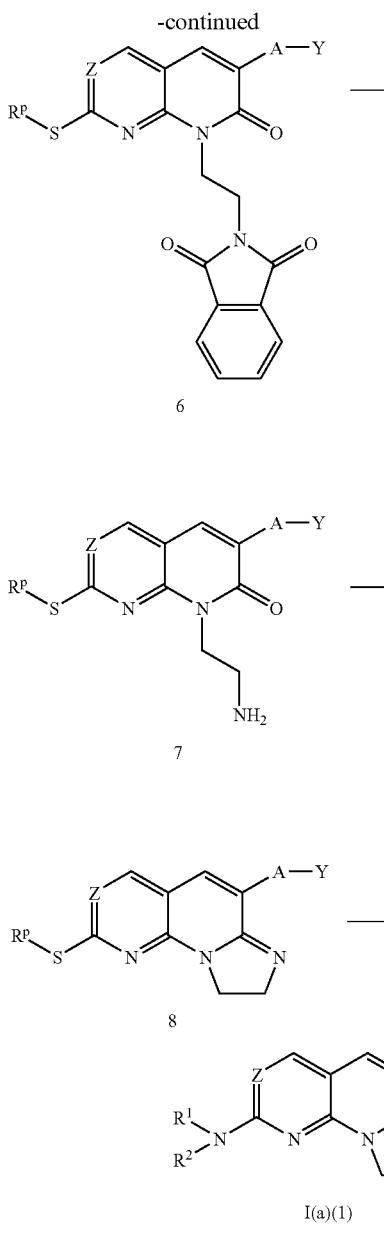

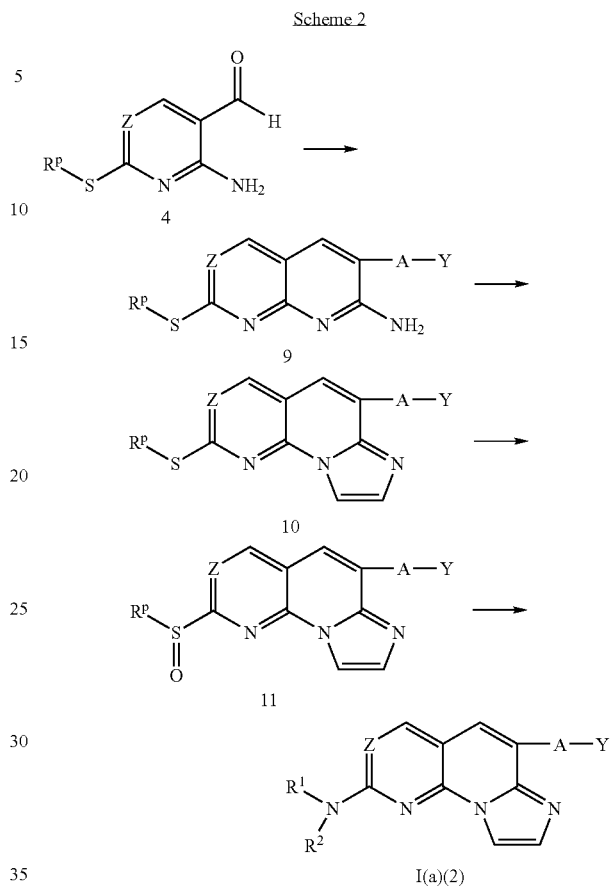

Scheme 2

Scheme 2 describes a general method of preparing a compound of formula I(a)(2) (compounds of formula I(a) wherein the dotted line is a bond), by starting with the aldehyde 4 from Scheme 1 above and heating it with a cyanide of general formula CN—CH$_2$-A-Y, wherein A and Y are as defined above, and potassium carbonate in DPMU to obtain aminopyridopyrimidine 9. Compound 9 is treated with triethylaamine and 1,2-dichloroethyl ethyl ether to afford sulfide of formula 10.

Compound 10 is then oxidized to the corresponding sulfoxide 11 by the method described in Scheme 1. The sulfoxide 11 is then reacted with the amine of formula —NH$^p$R$^1$R$^2$ to afford a compound of general formula I(a). Alternatively, sulfide 10 can be reacted directly with —NH$^p$R$^1$R$^2$ to afford a compound of general formula I(a)(2).

Scheme 3 describes a general method of preparing compound of formula I(c) starting with compound 12. Compound 12 is prepared according to the method described in WO 0129042 and WO 0129041.

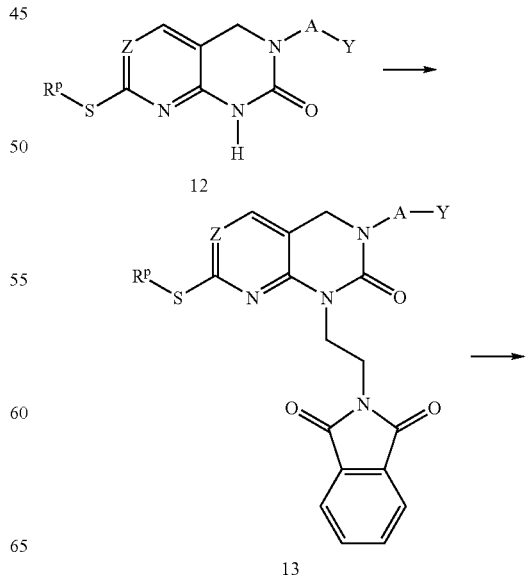

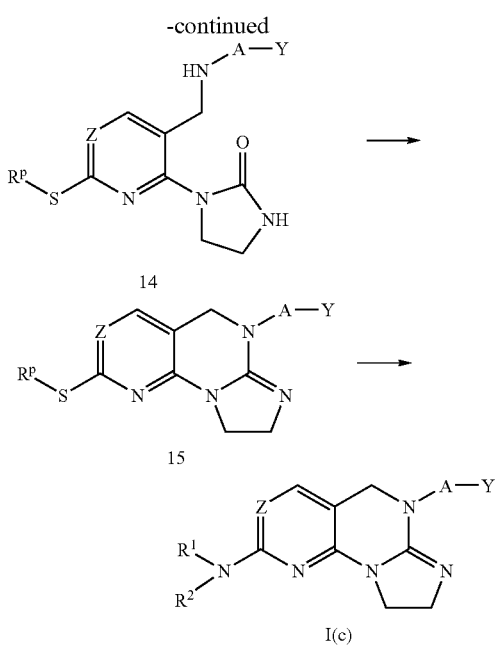

Compound 12 is treated with triphenylphosphine, diethylazodicarboxylate and N-(2-hydroxyethyl)-phthalimide to obtain compound 13. Compound 13 is then reacted with hydrazine hydrate to obtain compound 14, which is then reacted with trimethylaluminum solution to obtain compound 15. Compound 15 is reacted with an amine of formula —H$_2$NR$^1$R$^2$ to obtain a compound of formula I(c). Alternatively, compound 15 can be oxidized with 3-chloroperbenzoic acid to obtain the corresponding sulfoxide (not shown) which is then reacted with amine —NR$^1$R$^2$ to obtain the desired compound of formula I (c).

Pharmaceutical Compositions Containing the Compounds

The compounds of formula I and the pharmaceutically acceptable salts of basic compounds of formula I with acids can be used as medicaments, e.g. in the form of pharmaceutical preparations. The pharmaceutical preparations can be administered enterally, e.g. orally in the form of tablets, coated tablets, dragées, hard and soft gelatine capsules, solutions, emulsions or suspensions, nasally, e.g. in the form of nasal sprays, or rectally, e.g. in the form of suppositories. However, they may also be administered parenterally, e.g. in the form of injection solutions.

The compounds of formula I and their aforementioned pharmaceutically acceptable salts can be processed with pharmaceutically inert, organic or inorganic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active ingredient no carriers are, however, usually required in the case of soft gelatine capsules. Suitable carriers for the production of solutions and syrups are, for example, water, polyols, sucrose, invert sugar, glucose and the like. Suitable carriers for suppositories are, for example, natural or hardened oils, waxes, fats, semi-liquid or liquid polyols and the like.

The pharmaceutical preparations can also contain preservatives, solubilizers, stabilizers, wetting agents, emulsifiers, sweeteners, colorants, flavorants, salts for varying the osmotic pressure, buffers, masking agents or antioxidants. They can also contain therapeutically valuable substances other than the compounds of formula I and their aforementioned pharmaceutically acceptable salts.

Medicaments which contain a compound of formula I or a pharmaceutically acceptable salt of a basic compound of formula I with an acid in association with a compatible pharmaceutical carrier material are also an object of the present invention, as is a process for the production of such medicaments which comprises bringing one or more of these compounds or salts and, if desired, one or more other therapeutically valuable substances into a galenical administration form together with a compatible pharmaceutical carrier.

As mentioned earlier, the compounds of formula I and their aforementioned pharmaceutically acceptable salts can be used in accordance with the invention as therapeutically active substances, especially as antiinflammatory agents or for the prevention of graft rejection following transplant surgery. The dosage can vary within wide limits and will, of course, be fitted to the individual requirements in each particular case. In general, in the case of administration to adults a convenient daily dosage should be about 0.1 mg/kg to about 100 mg/kg, preferably about 0.5 mg/kg to about 5 mg/kg. The daily dosage may be administered as a single dose or in divided doses and, in addition, the upper dosage limit referred to earlier may be exceeded when this is found to be indicated.

Finally, the use of compounds of formula I and their aforementioned pharmaceutically acceptable salts for the production of medicaments, especially in the treatment or prophylaxis of inflammatory, immunological, oncological, bronchopulmonary, dermatological and cardiovascular disorders, in the treatment of asthma, central nervous system disorders or diabetic complications or for the prevention of graft rejection following transplant surgery, is also an object of the invention.

Methods of Using the Compounds and Compositions

Compounds of Formula I would be useful for, but not limited to, the treatment of any disorder or disease state in a human, or other mammal, which is exacerbated or caused by excessive or unregulated TNF or p38 kinase production by such mammal. Accordingly, the present invention provides a method of treating a cytokine-mediated disease which comprises administering an effective cytokine-interfering amount of a compound of Formula I, or a pharmaceutically acceptable salt or tautomer thereof.

Compounds of Formula I would be useful for, but not limited to, the treatment of inflammation in a subject, and for use as antipyretics for the treatment of fever. Compounds of the invention would be useful to treat arthritis, including but not limited to, rheumatoid arthritis, spondyloarthropathies, gouty arthritis, osteoarthritis, systemic lupus erythematosus (SLE) and juvenile arthritis, and other arthritic conditions. Such compounds would be useful for the treatment of pulmonary disorders or lung inflammation, including adult respiratory distress syndrome, pulmonary sarcoidosis, asthma, silicosis, and chronic pulmonary inflammatory disease. The compounds are also useful for the treatment of viral and bacterial infections, including sepsis, septic shock, gram negative sepsis, malaria, meningitis, cachexia secondary to infection or malignancy, cachexia secondary to acquired immune deficiency syndrome (AIDS), AIDS, ARC (AIDS related complex), pneumonia, and herpes virus. The compounds are also useful for the treatment of bone resorption diseases, such as osteoporosis, endotoxic shock, toxic shock syndrome, reperfusion injury, autoimmune disease including graft vs. host reaction and allograft rejections, cardiovascular diseases including atherosclerosis, thrombosis, congestive heart failure, and cardiac reperfusion injury, renal reperfusion injury, liver disease and nephritis, and myalgias due to infection.

The compounds are also useful for the treatment of influenza, multiple sclerosis, cancer, diabetes, skin-related conditions such as psoriasis, eczema, burns, dermatitis, keloid formation, and scar tissue formation. Compounds of the invention also would be useful to treat gastrointestinal conditions such as inflammatory bowel disease, Crohn's disease, gastritis, irritable bowel syndrome and ulcerative colitis. The compounds would also be useful in the treatment of ophthalmic diseases, such as retinitis, retinopathies, uveitis, ocular photophobia, and of acute injury to the eye tissue. Compounds of the invention also would be useful for treatment of angiogenesis, including neoplasia; metastasis; ophthalmological conditions such as corneal graft rejection, ocular neovascularization, retinal neovascularization including neovascularization following injury or infection, diabetic retinopathy, retrolental fibroplasia and neovascular glaucoma; ulcerative diseases such as gastric ulcer; pathological, but non-malignant, conditions such as hemangiomas, including infantile hemangiomas, angiofibroma of the nasopharynx and avascular necrosis of bone; diabetic nephropathy and cardiomyopathy; and disorders of the female reproductive system such as endometriosis. The compounds of the invention may also be useful for preventing the production of cyclo-oxygenase-2.

Besides being useful for human treatment, these compounds are also useful for veterinary treatment of companion animals, exotic animals and farm animals, including mammals, rodents, and the like. More preferred animals include horses, dogs, and cats.

The present compounds may also be used in co-therapies, partially or completely, in place of other conventional anti-inflammatories, such as together with steroids, cyclooxygenase-2 inhibitors, NSAIDs, DMARDS, immunosuppressive agents, 5-lipoxygenase inhibitors, $LTB_4$ antagonists and $LTA_4$ hydrolase inhibitors.

As used herein, the term "TNF mediated disorder" refers to any and all disorders and disease states in which TNF plays a role, either by control of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disorder mediated by TNF.

As used herein, the term "p38 mediated disorder" refers to any and all disorders and disease states in which p38 plays a role, either by control of p38 itself, or by p38 causing another factor to be released, such as but not limited to IL-1, IL-6 or IL-8. A disease state in which, for instance, IL-1 is a major component, and whose production or action, is exacerbated or secreted in response to p38, would therefore be considered a disorder mediated by p38.

As TNF-β has close structural homology with TNF-α (also known as cachectin), and since each induces similar biologic responses and binds to the same cellular receptor, the synthesis of both TNF-α and TNF-β are inhibited by the compounds of the present invention and thus are herein referred to collectively as "TNF" unless specifically delineated otherwise.

EXAMPLES

The following preparations and examples are given to enable a person of ordinary skill in the art to more clearly understand and practice the invention. The examples should not be considered as limiting the scope of the invention, but merely as being illustrative and representative thereof.

Example 1

Compound #12

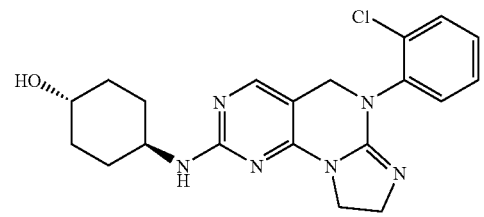

This example illustrates preparation of compound of formula I(c).

Step 1

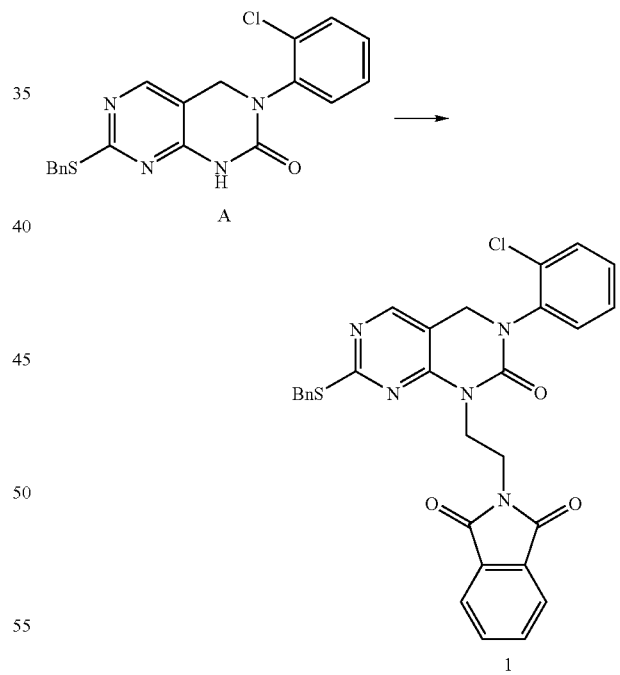

To a suspension of 3.0 g (7.84 mmol) of pyrimidinone A, 4.12 g (15.7 mmol) of triphenylphosphine and 4.12 g (15.7 mmol) of N-(2-hydroxyethyl)-phthalimide in 45 mL of 1,4-dioxane at 5° C. was added dropwise a solution of 2.73 g (2.5 mL, 15.7 mmol) of diethylazodicarboxylate in 10 mL of 1,4-dioxane over a period of 20 min. through an additional funnel. The suspension was stirred at 5° C. for 1 hour and then at room temperature overnight at which point the suspension turned into a yellow solution. The solution was concentrated in vacuo and the residue was purified by column chromatography with silica eluting with 7.5% ethyl acetate in dichloromethane affording 3.92 g of the phthalimide 1 (90% yield).

Step 2

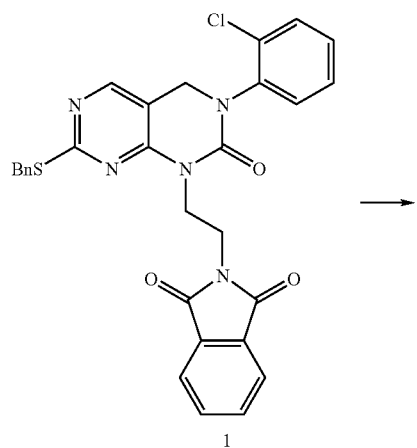

1

A mixture of 1.5 g (2.7 mmol) of the phthalimide 1 from Step 1 was stirred with 2.0 mL of hydrazine hydrate in 100 mL of methanol overnight at room temperature. The solution was concentrated in vacuo and the residue was partitioned between chloroform and water. The chloroform solution was washed with brine, dried (MgSO$_4$) and concentrated. The product was purified by column chromatography with silica eluting with 10% methanol in dichloromethane affording 1.0 g of the intermediate 2 (87% yield).

Step 3

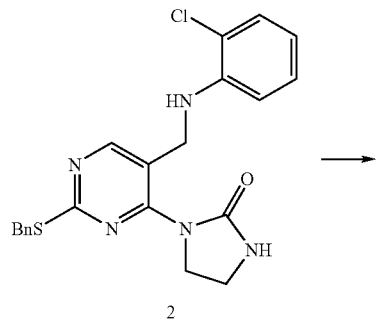

2

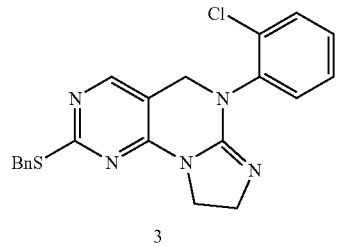

3

To a solution of 1.56 g (3.7 mmol) of compound 2 in 30 mL of toluene was added dropwise 2.3 mL of trimethylaluminum solution (2M in toluene, 4.6 mmol). The reaction mixture was heated to reflux for one hour until completion. The toluene was removed in vacuo and the residue was quenched with 100 mL of saturated aqueous NH$_4$Cl and 100 g of ice. 200 mL of ethyl acetate was added and the mixture was filtered. The solid collected was again mixed with 200 mL of ethyl acetate and 200 mL of water. This was stirred for 15 minutes and filtered. This operation was repeated one more time. All three filtrates were combined and transferred to a separatory funnel and the layers were separated. The aqueous layer was extracted once more with ethyl acetate. The combined ethyl acetate solution (about 800 mL) was washed with brine and dried (MgSO$_4$) and removed in vacuo affording 1.4 g of the tricyclic compound 3 (light yellow solid, 94% yield).

Step 4

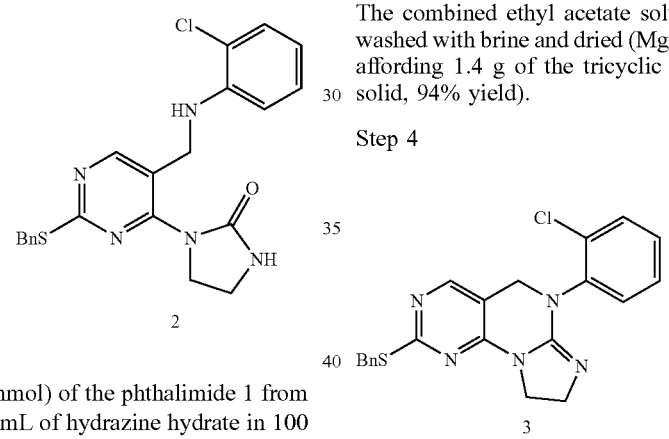

Compound 12

A solution of 0.171 g (0.42 mmol) of tricyclic-sulfide 3 in 20 mL of dichloromethane was cooled to 5° C. 0.094 g (0.42 mmol) of 3-chloroperbenzoic acid (77% max.) was added. The mixture was stirred for 30 minutes until completion and the solution was poured in saturated aqueous Na$_2$SO$_3$, extracted with dichloromethane (2×75 mL). The dichloromethane was then washed with cold saturated aqueous NaHCO$_3$, brine and dried (MgSO$_4$). The solvent was removed in vacuo recovering 0.17 g of the sulfoxide (96% yield). This sulfoxide was mixed with 0.21 g (1.8 mmol) of trans-4-aminocyclohexanol and 1 mL of NMP was heated in a 120° C. oil bath for 45 minutes until reaction was completed. The mixture was diluted with water and extracted with ethyl acetate (3×30 mL). The combined ethyl acetate solution was then washed with water (3×30), brine, and dried (MgSO$_4$). The solvent was removed in vacuo and residue recovered was purified by column chromatography with silica eluting with MeOH/CH$_2$Cl$_2$/Et$_3$N (1/9/0.4), affording 19 mg of compound 13. (mass spec. M+1=399)

Example 2

Compound 13

This example illustrates the preparation of compound of formula I (a) following the procedure described in Scheme 1.

Step 1

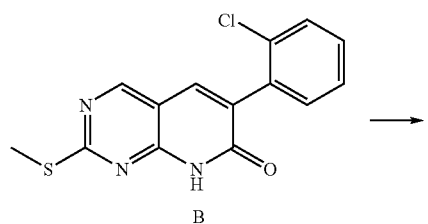

B

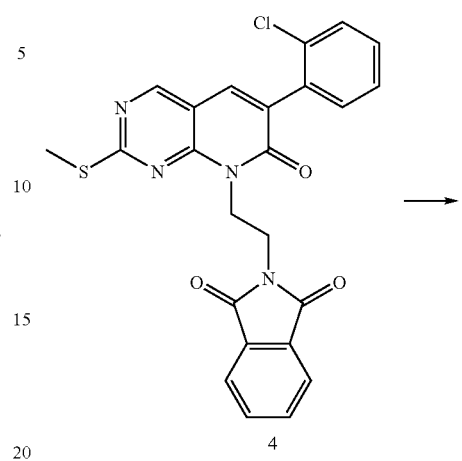

4

To a suspension of 3.0 g (9.88 mmol) of pyridone B, 5.18 g (19.8 mmol) of triphenylphosphine and 3.78 g (19.8 mmol) of N-(2-hydroxyethyl)-phthalimide in 45 ml of 1,4-dioxane at 5° C. was added dropwise a solution of 2.73 g (2.5 ml, 15.7 mmol) of diethylazodicarboxylate in 10 ml of 1,4-dioxane over a period of 20 min. through an additional funnel. The suspension was then stirred at 5° C. for 1 hour and then at room temperature overnight. The suspension was filtered and the solid was washed with methanol, then ether. The white solid, 2.17 g was the desired material. The filtrate was concentrated and purified by column chromatography with silica eluting with 5% ethyl acetate in hexanes affording another 1.2 g of the desired product. Total yield of 4 was 71%.

Step 2

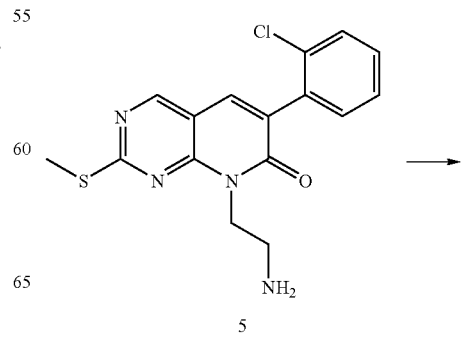

To a suspension of 1.2 g (2.5 mmol) of phthalimide 4 in 100 ml of methanol was added 6 ml of hydrazine monohydrate. This was stirred at room temperature overnight upon which the suspension turned into a clear yellow solution. The mixture was concentrated and residue was diluted with water and extracted with chloroform. The organic solution was washed with brine and dried (MgSO$_4$), and the residue was purified by column chromatography with silica eluting with 10% methanol in dichloromethane affording 0.48 g of the aminoethyl-pyridone 5 (55% yield).

Step 3

-continued

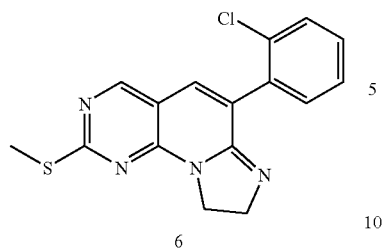

To a solution of 0.48 g (1.4 mmol) of compound 5 in 10 mL of toluene was added dropwise 0.87 mL of trimethylaluminum solution (2M in toluene, 1.76 mmol). The reaction mixture was heated to reflux for two hours until completion. The toluene was removed in vacuo and the residue was quenched with 50 mL of saturated aqueous NH$_4$Cl and was extracted with ethyl acetate (3×75 mL). The combined organic solution was washed with brine and dried (MgSO$_4$) and removed in vacuo affording 0.36 g of the tricyclic compound 6 (80% yield).

Step 4

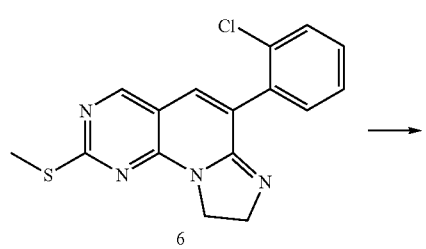

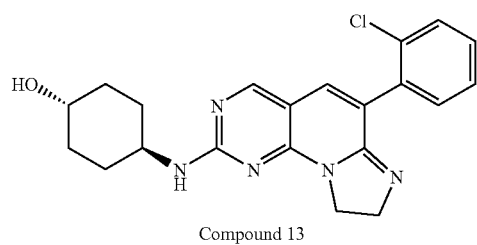

Compound 13

A mixture of 0.1 g (0.3 mmol) of compound 6 and 0.325 g (1 mmol) of trans-4-aminocyclohexanol in 0.5 mL of NMP was heated in a 200° C. sand-bath (heating mantle) for 14 hours. After cooling the mixture was diluted with water and extracted with ethyl acetate (3×50 mL). The combined organic solution was washed with water (3×50 mL), brine and dried (MgSO$_4$). The solvent was removed in vacuo and the product was purified by column chromatography with silica eluting with a gradient of 5% to 20% methanol in dichloromethane affording 0.102 g of compound 13. (mass spec. M+1=396, MP=169.3-175.8° C.).

Example 3

Compound 1

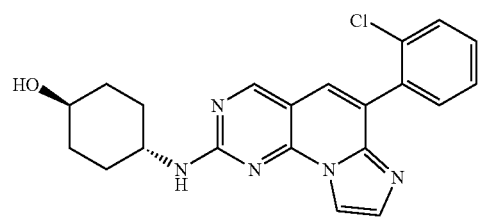

Step 1

4-amino-2-benzylsulfanyl-pyrimidine-5-carboxylate

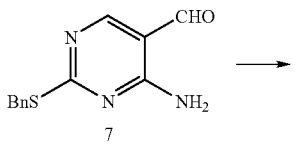

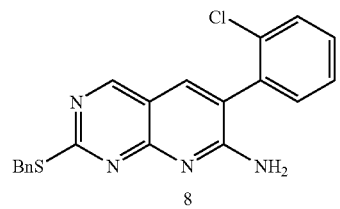

A mixture of 5 g (20.4 mmol) of aldehyde 7, 3.71 g (24.4 mmol) of 2-chlorobenzylcyanide and 18 g (130 mmol) of potassium carbonate in 50 mL of DMPU was heated in a 110° C. oil bath for 3 hours until the reaction was completed. The mixture was poured into 600 ml of water and extracted with 300 mL of ethyl acetate. The organic solvent was washed with water (3×250 mL), diluted with 200 mL of hexanes, washed with brine, dried (MgSO$_4$), and filtered through a short plug of silica. The solvent was removed in vacuo. Residual solid was stirred in 50 mL of ethyl acetate for 30 minutes. The solid was filtered off and washed with small amount of ethyl acetate, recovering 2.23 g of the aminopyridopyrimidine 8. The filtrate was concentrated and the residue was purified by column chromatography with silica eluting with 50% ethyl acetate in hexanes, isolating an additional 0.62 g of 2-benzylsulfanyl-6-(2-chloro-phenyl)-pyrido[2,3-d]pyrimidin-7-ylamine 8 (total yield: 37%).

Step 2

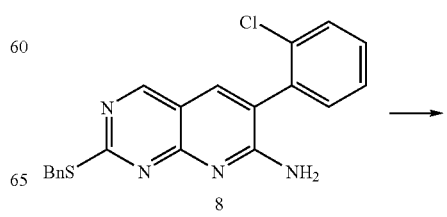

-continued

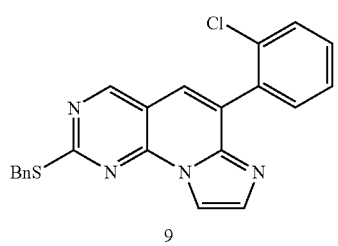

9

To a mixture of 3 g (7.9 mmol) of amine 8, 4.8 g (6.6 mL, 47.6 mmol) of triethylamine, 5 mL of water and 50 mL of acetonitrile was added a total of 4.0 mL (32 mmol) of 1,2-dichloroethyl ethyl ether over a period of 6 hours (1 equivalent/hour the first two hours and 0.5 equivalent/hour the following four hours), until reaction was completed. The mixture was allowed to stand overnight at room temperature, diluted with water and extracted with ethyl acetate (2×100 mL). The organic solution was washed with brine and dried (MgSO$_4$) and removed in vacuo. Purification was done by column chromatography with silica eluting with 30% ethyl acetate in hexanes affording 2 g of the sulfide 9 (63% yield).

Step 3

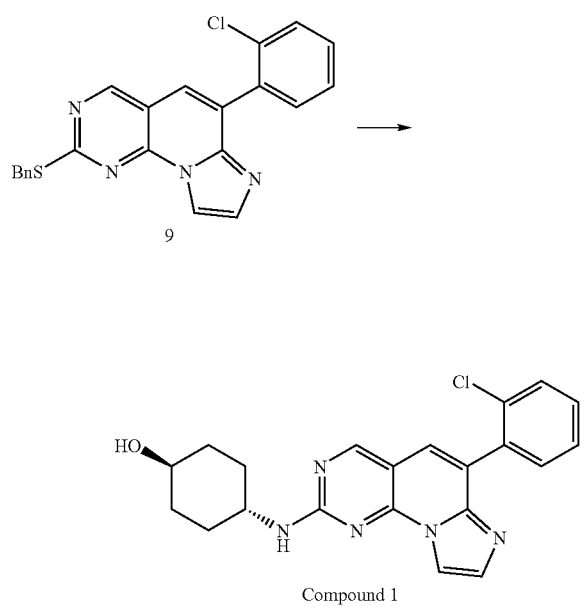

A mixture of 0.056 g (0.14 mmol) of compound 9 and 0.053 g (0.46 mmol) of trans-4-aminocyclohexanol in 1 mL of NMP was heated in a 205° C. sand-bath (heating mantle) for 14 hours. After cooling the mixture was diluted with water and extracted with ethyl acetate (3×50 mL). The combined organic solution was washed with water (3×50 mL), brine and dried (MgSO$_4$). The solvent was removed in vacuo affording 0.39 g of the desired compound 1 (Compound 1). (mass spec. M+1=394, MP=116-119° C.).

Step 4

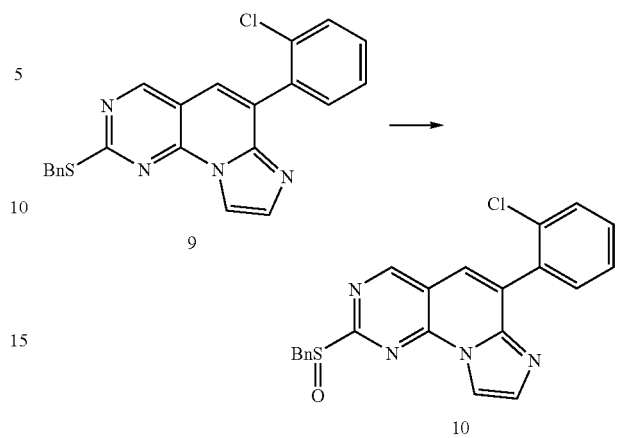

Optionally, to a cooled solution of 2 g (5 mmol) of the sulfide 9 in 60 mL of dichloromethane at 5° C. was added 1.11 g (5 mmol) of 3-chloroperbenzoic acid (77% max.). The reaction was completed in 3 hours and the mixture was poured into saturated aqueous NaHCO$_3$ and extracted with dichloromethane. The organic solution was then washed with 10% aqueous NaHSO$_3$, brine and dried (MgSO$_4$). After removal of solvent in vacuo, 2 g of the sulfoxide 10 was recovered. (96% yield). The corresponding methylsulfoxide (substituting Bn for Me) was prepared in a similar manner. The sulfoxide 10 was then converted into compound #1 as described in Step 4 above.

Example 4

Compound 3

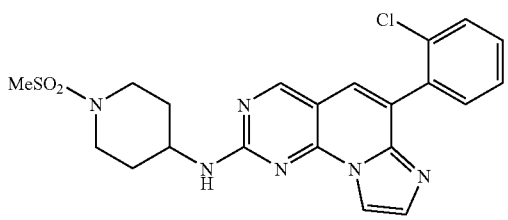

Preparation of 1-(methylsulfonyl)piperidine-4-amine (15)

Step 1

Benzyl 1-benzylpiperidin-4-ylcarbamate

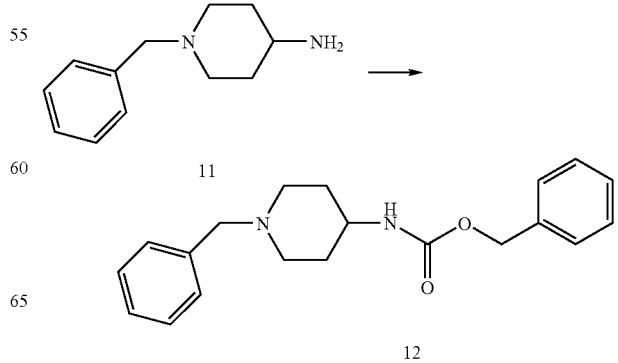

To a 0° C. solution of 4-amino-1-benzylpiperidine 11 (41.2 g, 216.5 mmol) and triethylamine (51.3 mL, 369 mmol) in 600 mL of tetrahydrofuran was added benzyl chloroformate (31 mL, 217 mmol) dropwise over a period of 30 to 45 min. at such a rate that the reaction temperature was kept between 5° C. and 10° C. After the addition was complete, the reaction mixture was allowed to warm to room temperature and stir for 12 hours. The solvent and volatiles were removed under reduced pressure. Water (500 mL) and ethyl acetate (1.2 L) were then added and the reaction was partitioned between the two phases. The organic layer was washed with saturated aqueous sodium bicarbonate solution (2×, 150 mL) and then dried (brine, MgSO$_4$). Evaporation of the solvent yielded a tan liquid which was purified via column chromatography (SiO$_2$, EtOAc/Hexane—30/70 to EtOAc—100) to provide 27.8 g of the amine 12 as a white solid (mass spec. M+=324, MP=79.1-79.6° C.).

Step 2

Benzyl piperidin-4-ylcarbamate

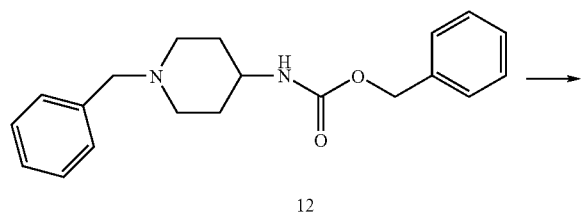

12

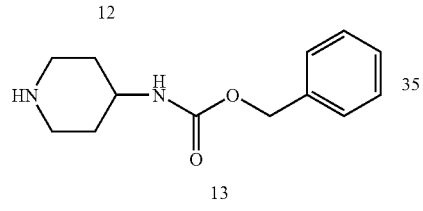

13

The benzyl amine 12 (27.8 g, 85.7 mmol) was dissolved in 400 mL of methylene chloride at room temperature and 1-chloro-ethylchloroformate (25.4 g, 178 mmol) in 50 mL of methylene chloride was added dropwise via addition funnel. After addition was complete, the reaction mixture was stirred at room temperature for 3 hours. The solvent and volatiles were removed under reduced pressure and methanol (500 mL) was added. The reaction was heated to reflux with stirring for 1 hour and then cooled to room temperature. Removal of the reaction solution via evaporation yielded 26.3 g of the piperidine 13 as an off-white solid (mass spec. M+1=235, MP=190.7-192.2° C.).

Step 3

Benzyl 1-(methylsulfonyl)piperidin-4-ylcarbamate

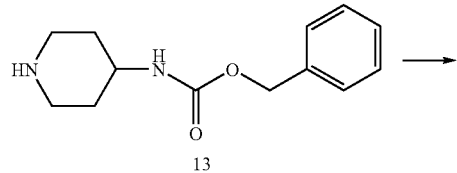

13

-continued

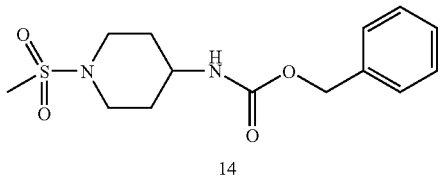

14

The protected piperidine 13 (10 g, 42.7 mmol) and triethylamine (12 mL, 86.7 mmol) was dissolved in 500 mL of methylene chloride at room temperature. Methane sulfonylchloride (4.3 mL, 55.5 mmol) in 20 mL of methylene chloride was added dropwise via addition funnel. After addition was complete, the reaction mixture was stirred at room temperature for 3 hours. The solvent and volatiles were removed under reduced pressure. Ethyl acetate (500 mL) and an aqueous solution of hydrochloric acid (0.5M, 350 mL) was added. The reaction was partitioned between the two phases and the aqueous layer was removed. The organic layer was washed again with an aqueous solution of hydrochloric acid (0.5M, 2×, 100 mL) and then with saturated aqueous sodium bicarbonate solution (3×, 100 mL). The reaction solvent was then dried (brine, MgSO$_4$) and evaporated at reduced pressure to provide 9.2 g of the methane sulfonamide 14 (MP=148.6-152.8° C.).

Step 4

1-(methylsulfonyl)piperidin-4-amine

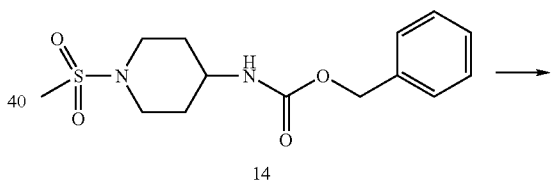

14

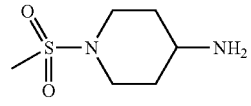

15

The methane sulfonamide 14 (9.2 g, 29.5 mmol) was dissolved in 200 mL of tetrahydrofuran at room temperature in a 500 mL round-bottomed flask under a nitrogen atmosphere. Palladium on Carbon (10%, 2-3 g) was then added and the reaction vessel was flushed with hydrogen gas (3×). A balloon of hydrogen gas was put on the reaction flask and the solution was stirred for 15 hours (more catalyst added and hydrogen balloon filled if necessary). Methylene chloride (100 mL) was added to the reaction and it was filtered through a celite pad. Evaporation of the solvents under reduced pressure provided 4.63 g of the desired amine 15 (mass spec. M+1=179, MP=65.3-65.7° C.).

Step 5

A mixture of 0.6 g (1.43 mmol) of sulfoxide 10 from Example 3 and 0.51 g (2.86 mmol) of the 1-(methylsulfonyl) piperidine-4-amine 15 in 1 mL of NMP was heated to 70 to 80° C. for 1 hour. This was cooled and diluted with water and extracted with ethyl acetate (2×75 mL). [Starting material 15 and product had the same Rf value on TLC (5% MeOH/CH$_2$Cl$_2$), mass spec. of reaction product: M+1=457)]. The organic solution was washed with water (2×75 mL), brine and dried (MgSO$_4$) and concentrated. The residue was purified by column chromatography eluting with 30% ethyl acetate in dichloromethane affording 0.473 g (73% yield) of product. This was dissolved in 1 mL of dichloromethane and 1.24 mL of 1M HCl/ether was added. The suspension was stirred for 30 minutes, filtered and washed with ether affording 0.47 g of compound 3. (mass spec. M+1=457, MP=188-194° C.)

Example 5

Compound 2

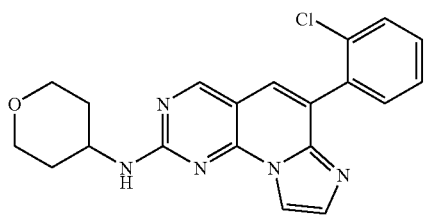

A mixture of 0.7 g (1.67 mmol) of sulfoxide 10 from Example 3 and 0.84 g (8.4 mmol) of 4-aminotetrahydropyran in 1 mL of NMP was stirred at 10 minutes. The reaction was exothermic and completed in 10 minutes. The mixture was diluted with water and extracted with ethyl acetate. The organic solution was washed with brine and dried (MgSO$_4$) and removed in vacuo. The purification was done by column chromatography with silica eluting with 60% ethyl acetate in hexanes affording 0.46 g (73% yield) of product. This solid in 1 mL of dichloromethane was mixed with 1.45 mL of 1M HCl/ether and the mixture was stirred for 1 hour. Solvent was removed in vacuo affording 0.48 g of compound 2. (mass spec. M+1=380, MP=211-214° C.)

Example 6

Compound 5

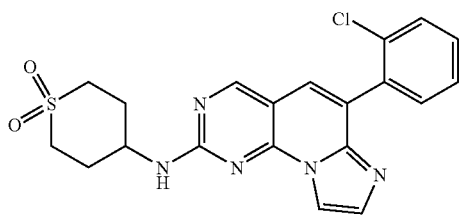

Preparation of 4-aminotetrahydrothiopyran-dioxide

Step 1

4-aminotetrahydrothiopyran

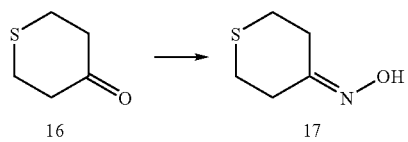

A suspension mixture of 5 g (0.043 mole) of tetrahydrothiopyran-4-one 16, 29.26 g (0.215 mole) of sodium acetate trihydrate and 14.9 g (0.215 mole) of hydroxylamine hydrochloride in 200 mL of ethanol was heated to reflux for six hours until reaction was completed. The reaction mixture was cooled and ethanol was removed under reduced pressure. The residue was diluted with 400 mL of ice water and was extracted with ethyl acetate, 3×150 mL. The organic solution was washed with brine, dried and filtered. The filtrate was concentrated under reduced pressure affording 5.6 g (quantitative yield) of the thianone oxime 17 (white solid).

Step 2

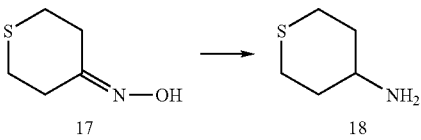

To 76 mL of 1M LAH/THF (0.076 mole) was added dropwise a solution of 2 g (0.015 mole) of thianone oxime 17 in 30 mL of THF. After addition was completed, the mixture was stirred under reflux for 7 hours and then at room temperature overnight. The suspension was cooled and 2.9 mL of water was added dropwise cautiously, followed by 2.9 mL of 15% aq. sodium hydroxide and then 8.7 mL of water. The suspension was stirred for 30 min., filtered over Celite and washed with 200 mL of ethyl acetate. The filtrate was dried, filtered and evaporated to dryness under reduced pressure (<50° C.) affording 1.62 g (92.3% yield) of the 4-aminotetrahydrothiopyran 18.

Step 3

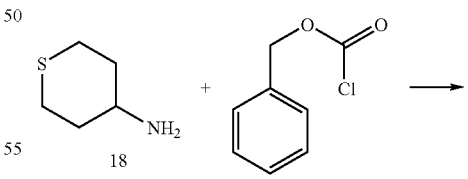

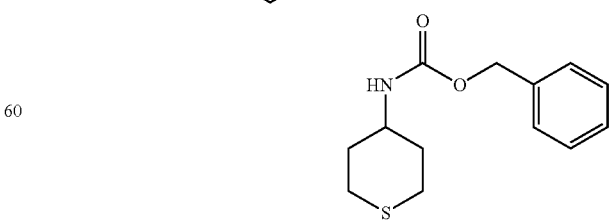

To a suspension of 2.3 g (0.0197 mole) of the 4-aminotetrahydrothiopyran 18 in 25 mL of 1N NaOH was added dropwise at 5° C. 3.14 mL (3.75 g, 0.022 mole) of benzyl-chloroformate. Solid formed immediately and after addition was completed, the mixture was stirred at room temperature for 1 hour, filtered and washed with water. This was followed by washing with hexane (50 mL). After drying (air dried), 4.4 g (88% yield) of product 19 was obtained. (mass spec. M+1=252).

Step 4

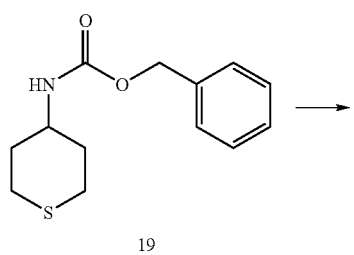

19

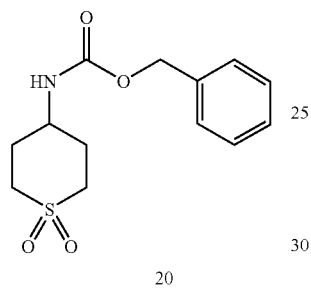

20

To a solution of 40 g (0.159 mole) of sulfide 19 in 200 mL of dichloromethane at room temperature was added in small portions of 75 g (0.33 mole) of 3-chloroperbenzoic acid. Reaction was exothermic. The reaction mixture was allowed to stir overnight. The mixture was washed with aqueous saturated $Na_2SO_3$ (2×150 mL) and then with $NaHCO_3$ (3×150 mL). The organic solution was then washed with brine and dried over $MgSO_4$. The mixture was filtered and the filtrate was evaporated in vacuo to afford 37.5 g of the sulfone 20 (83% yield).

Step 5

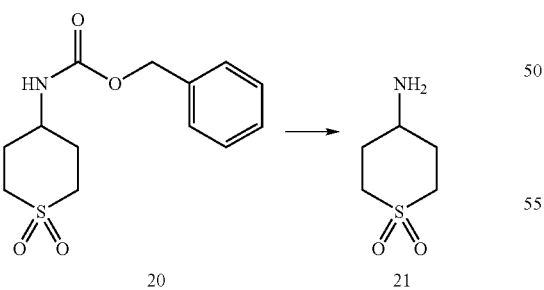

20                    21

To a mixture of 10 g (0.026 mole) of the N-benzoyloxy-carbonyl-sulfone 20 in 150 mL of ethanol in a Parr bottle was added 0.5 g of palladium hydroxide (20% on Carbon, Pearlman's catalyst). This was subjected to the Parr hydrogenator at 50 psi for 15 hours until completion. This was filtered over Celite and concentrated in vacuo affording 5.0 g of the free amine 21 (68% yield).

Step 6

A mixture of 1.4 g (0.41 mmol) of sulfoxide 10 and 1.22 g (8.2 mmol) of 4-aminotetrahydrothiopyran-dioxide 21 in 3 mL of NMP was heated to 70° C. for 2 hours. The mixture was cooled, diluted with water and extracted with ethyl acetate (2×75 mL). The combined ethyl acetate solution was washed with water (3×75 mL), brine and dried ($MgSO_4$) and the crude material was purified by column chromatography with silica eluting with 4% methanol in dichloromethane affording 1.5 g of desired product. This was dissolved in 3 mL of dichloromethane and 4.5 mL of 1M HCl/ether was added dropwise. The suspension was stirred for 30 minutes and the solid was filtered and washed with ether affording 1.86 g (98% yield) of compound 5. (mass spec. M+1=428, MP=221.8-226.8° C.).

Example 7

Compound 6

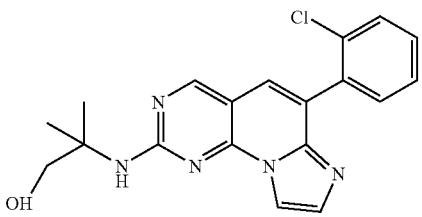

A mixture of 0.4 g (1.2 mol) of sulfoxide 10 and 0.52 g (5.8 mmol) of 2-amino-2-methyl-1-propanol in 10 ml of chloroform and 0.8 ml of nmp was heated to 70° C. for 3 hours. The chloroform was removed under reduced pressure. 40 ml of methanol/ether (1:1) was added. The suspension was stirred for 10 minutes and was filtered. The solid was washed with more ether affording 0.258 g (58.5% yield) of desired product. This was dissolved in 15 ml of 10% methanol in dichloromethane and 0.85 ml of 1M HCl/ether was added. The mixture was stirred for 30 minutes and concentrated. Ether was added and the solid was filtered and washed with ether affording 0.295 g of compound 6. (mass spec. M+1=368, MP=190.8-194.3° C.

Example 8

Compound 7

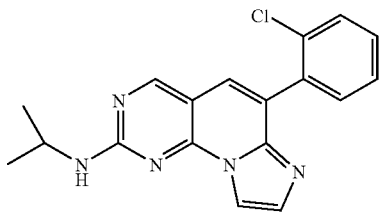

A glass sealed-tube (teflon screw cap) reactor was charged with 0.4 g (1.2 mmol) of the sulfoxide 10. This was purged with nitrogen for 2 minutes as the reaction vessel was cooled with an ice-water bath. 5 ml of isopropyl amine was added and the tube was sealed. The red solution was heated in a 64° C. oil bath for 2 hours until reaction was completed. The mixture was cooled and the reaction vessel was rinsed with dichloromethane. The solvent was removed in vacuo and the sample was purified by column chromatography with silica eluting with a gradient of 5 to 10% ethyl acetate in dichloromethane affording 0.34 g (87% yield) of product. This light yellow solid was dissolved in a minimum amount of dichloromethane and 1.2 ml of 1M HCl/ether was added, followed by 5 ml of ether. The yellow suspension was stirred for 1 hour and was filtered and washed with ether affording 0.34 g of compound 7. (Mass Spec. M+1=338, MP=210-212.5° C.)

Example 9

Compound 8

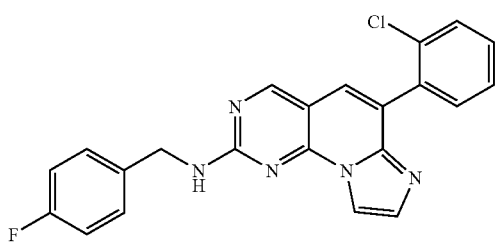

A mixture of 0.4 g (1.2 mmol) of sulfoxide 10 and 0.29 g (2.33 mmol) of 4-fluorobenzylamine in 5 mL of chloroform was heated in a 60° C. oil bath for 1.5 hours until reaction was completed. The product was purified directly by column chromatography eluting with a gradient of 5 to 10% ethyl acetate in dichloromethane affording 0.42 g (89% yield) of the product. The yellow solid was dissolved in a minimum amount of dichloromethane, and 1.25 mL of 1M HCl/ether was added. The mixture was stirred for 30 minutes and solvent was removed in vacuo. Ether was added and the solid was filtered and washed with ether affording 0.469 g of compound 8. (mass spec. M+1=404, MP=178-180° C.)

Example 10

Compound 9

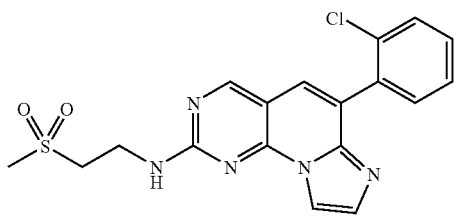

A mixture of 0.4 g (1.2 mmol) of sulfoxide 10 and 0.36 g (2.4 mmol) of 2-aminoethyl methyl sulfone in 3 mL of NMP was heated to 65° C. for 30 minutes. [2-aminomethyl sulfone was prepared by reacting 4-methoxybenzylamine with methyl vinyl sulfone in presence of triethylamine in THF at room temperature, the N-benzyl group was removed by stirring in methanol in presence of ammonium formate and 10% Pd-C]. The mixture was cooled, diluted with water and ethyl acetate. The solid formed was filtered, washed with more ethyl acetate and then 40 mL of methanol affording 0.34 g (72.6% yield) of product. This was dissolved in 5 mL of 10% methanol in dichloromethane and 1 mL of 1M HCl/ether was added. Stirring was continued for 30 minutes and solvent was removed in vacuo. Ether was added for trituration and the solid formed was filtered and washed with additional 10 mL of ether affording 0.374 g of compound 9. (mass spec. M+1=402, MP=172.2-176° C.)

Example 11

Compound 10

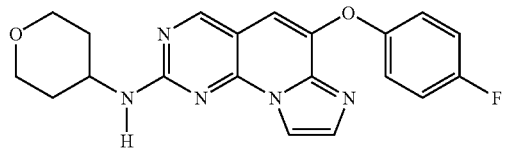

Step 1

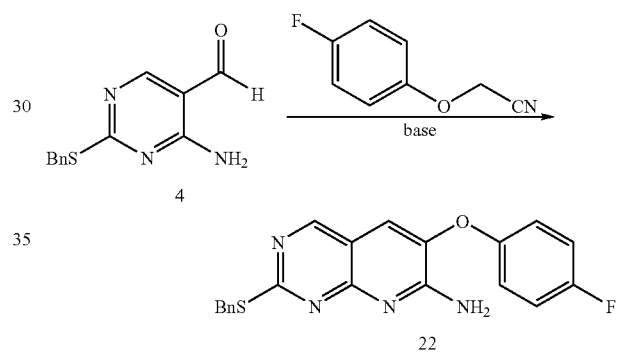

A mixture of 2.48 g (10.1 mmol) of aldehyde 4 from example 2, 1.83 g (12 mmol) of 4-fluorophenoxyacetonitrile (prepared from 4-fluorophenol and iodoacetonitrile in $K_2CO_3$/DMF) and 7 g (50.6 mmol) of potassium carbonate in 30 mL of NMP was heated at 110° C. for 4 hours until the reaction was completed. The mixture was poured into 200 ml of water and extracted with ethyl acetate (3×125 mL). The organic solvent was washed with water (3×150 mL), brine, diluted with 200 mL of hexanes, dried (MgSO$_4$) and filtered through a short plug of silica. The solvent was removed in vacuo. Residual solid was purified by column chromatography with silica eluting with a gradient of 5% to 20% ethyl acetate in dichloromethane, affording 1.3 g of the aminopyridopyrimidine 22, (37% yield). (mass spec. M+1=379, MP=186.2-192.9° C.)

Step 2

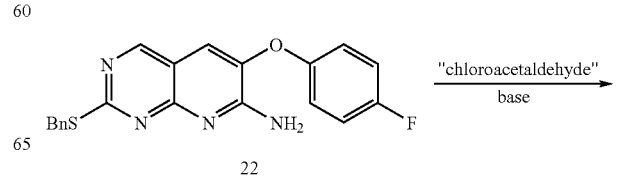

-continued

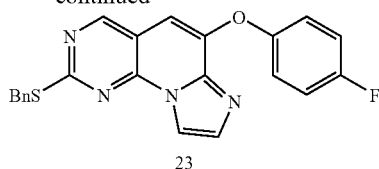

23

To a mixture of 1.3 g (3.4 mmol) of amine 22, 1.54 g (2.1 mL, 15.3 mmol) of triethylamine, 3 mL of water and 30 mL of acetonitrile was added a total of 2.4 mL (19.6 mmol, 5.8 eq) of 1,2-dichloroethyl ethyl ether over a period of 6 hours (1 equivalent/hour the first two hours and 0.5 equivalent/hour the following four hours), until the reaction was completed. The mixture was allowed to stand overnight at room temperature, diluted with water and extracted with ethyl acetate (2×100 mL). The organic solution was washed with brine and dried (MgSO$_4$) and removed in vacuo. Purification was done by column chromatography with silica eluting with 10% ethyl acetate in hexanes affording 0.78 g (57% yield) of the phenoxy-tricyclic-imidazole 23 (57% yield).

Step 3

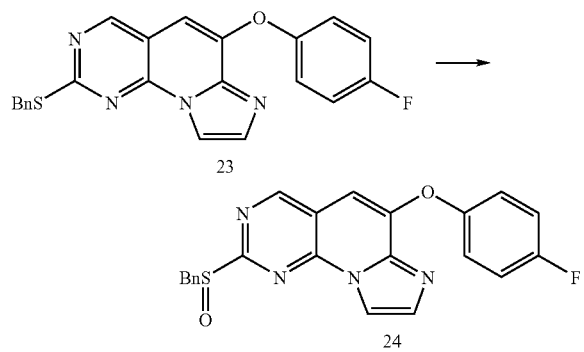

To a cooled solution of 0.77 g (1.92 mmol) of the sulfide 23 in 30 mL of dichloromethane at 5° C. was added 0.43 g (1.92 mmol) of 3-chloroperbenzoic acid (77% max.). The reaction was completed in 1 hour and the mixture was poured into cold saturated aqueous NaHCO$_3$ and extracted with dichloromethane. The organic solution was washed with brine and dried (MgSO$_4$). After removal of solvent in vacuo, 0.763 g of the sulfoxide was recovered (95% yield).

Step 4

A mixture of 0.4 g (0.96 mmol) of sulfoxide 24 and 0.48 g (4.78 mmol) of 4-aminotetrahydropyran in 1 mL of NMP was heated at 60 to 70° C. for 30 minutes. The mixture was diluted with water and extracted with ethyl acetate. The organic solution was washed with brine and dried (MgSO$_4$) and removed in vacuo. The purification was done by column chromatography with silica eluting with a gradient of 10 to 30% ethyl acetate in dichloromethane to elute out the non-polar impurities and finally with 2.5% methanol in dichloromethane to elute out the product, 0.210 g (58% yield). This solid in 1 mL of dichloromethane was mixed with 0.83 mL of 1M HCl/ether and the mixture was stirred for 1 hour, diluted with ether and filtered affording 0.21 g of compound 10. (mass spec. M+1=380, MP=198-206° C.)

Example 12

Compound 11

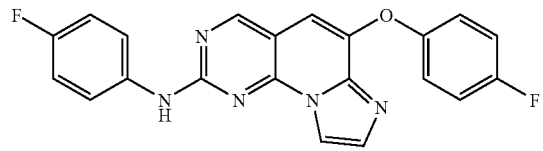

To 0.11 g (1.0 mmol) of 4-fluoroaniline in 5 ml of dichloromethane at 5° C. was added 0.5 ml (1.0 mmol) of trimethylaluminum reagent (2M/toluene) dropwise. After addition, stirring was continued for 10 minutes. This solution was then added through a syringe to a solution of 0.355 g (0.85 mmol) of sulfoxide from Example 10 in 10 ml of dichloromethane at 5° C. The mixture was then stirred at 17 hours and then at reflux for 3 hours. This was poured into saturated aqueous NH$_4$Cl solution. The mixture was filtered and the filtrate was transferred to a separatory funnel as the layers were separated. The aqueous layer was extracted once more with dichloromethane and the combined organic solution was washed with brine and dried (brine, MgSO$_4$). After removal of solvent in vacuo, the residue was purified by column chromatography with silica eluting with 10% ethyl acetate in dichloromethane affording 0.16 g of yellow solid. This was mixed with 5 ml of 20% methanol in dichloromethane and 0.49 ml of 1M HCl/ether was added. This was stirred for 30 minutes and solvent was evaporated to dryness. 10 ml of ether was added and the yellow suspension was stirred for 10 minutes, filtered and washed with additional ether affording 0.145 g of compound 11. (mass spec. M+1=390, mp=289.3-291.1° C.)

One of skill in the art will understand that certain modifications to the above schemes are contemplated and within the scope of the present invention. For example, certain steps will involve the use of protecting groups for functional groups that are not compatible with particular reaction conditions.

Example 13

The following are representative pharmaceutical formulations containing a compound of Formula (I).

Tablet Formulation

The following ingredients are mixed intimately and pressed into single scored tablets.

| Ingredient | Quantity per tablet, mg |
|---|---|
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule, mg |
| --- | --- |
| compound of this invention | 200 |
| lactose, spray-dried | 148 |
| magnesium stearate | 2 |

Suspension formulation
The following ingredients are mixed to form a suspension for oral administration.

| Ingredient | Amount |
| --- | --- |
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| Sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Injectable Formulation

The following ingredients are mixed to form an injectable formulation.

| Ingredient | Amount |
| --- | --- |
| compound of this invention | 0.2 g |
| sodium acetate buffer solution, 0.4 M | 2.0 ml |
| HCl (1N) or NaOH (1N) | q.s. to suitable pH |
| water (distilled, sterile) | q.s. to 20 ml |

All of the above ingredients, except water, are combined and heated to 60-70° C. with stirring. A sufficient quantity of water at 60° C. is then added with vigorous stirring to emulsify the ingredients, and water then added q.s. to 100 g.

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| compound of the invention | 500 mg |
| --- | --- |
| Witepsol ® H-15 | balance |

Example 14

Inhibition of p-38 (MAP) Kinase. In Vitro Assay

The p-38 MAP kinase inhibitory activity of compounds of this invention in vitro was determined by measuring the transfer of the γ-phosphate from γ-$^{33}$P-ATP by p-38 kinase to Myelin Basic Protein (MBP), using the a minor modification of the method described in Ahn, N. G.; et al. *J. of Biol. Chem.* Vol. 266(7), 4220-4227, (1991)

The phosphorylated form of the recombinant p38 MAP kinase was expressed with SEK-1 and MEKK in *E. Coli* (see, Khokhlatchev, A. et al. *J. of Biol. Chem.* Vol. 272(17), 11057-11062, (1997) and then purified by affinity chromatography using a Nickel column.

The phosphorylated p38 MAP kinase was diluted in kinase buffer (20 mM 3-(N-morpholino)propanesulfonic acid, pH 7.2, 25 mM β-glycerol phosphate, 5 mM ethylene glycol-bis(beta-aminoethyl ether)-N,N,N',N'-tetraacetic acid, 1 mM sodium vanadate, 1 mM dithiothreitol, 40 mM magnesium chloride). Test compound dissolved in DMSO or only DMSO (control) was added and the samples were incubated for 10 min. at 30° C. The kinase reaction was initiated by the addition of a substrate cocktail containing MBP and γ-$^{33}$P-ATP. After incubating for an additional 20 min. at 30° C., the reaction was terminated by adding 0.75% phosphoric acid. The phosphorylated MBP was then separated from the residual γ-$^{33}$P-ATP using a phosphocellulose membrane (Millipore, Bedford, Mass.) and quantitated using a scintillation counter (Packard, Meriden, Conn.).

The p-38 inhibitory activities (expressed as IC$_{50}$, the concentration causing 50% inhibition of the p-38 enzyme being analyzed) of the compounds listed in Table 1 in the specification are between 0.001 µM and 10 µM. For example, Table 2, below, shows representative values for inhibition of p38 using the Ex. 14 assay:

TABLE 2

| Ex. No. | IC$_{50}$ µM | Ex. No. | IC$_{50}$ µM |
| --- | --- | --- | --- |
| 1 (cpd. #12) | 6.62 | 4 (cpd #3) | 0.0027 |
| 2 (cpd. #13) | 1.14 | 7 (cpd #6) | 0.0188 |
| 3 (cpd. 1) | 0.01 | 8 (cpd #7) | 0.0014 |

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All publications, patents, and patent applications cited herein are hereby incorporated by reference in their entirety for all purposes.

What is claimed is:

1. A compound represented by formula I:

(I)

wherein:
- Z is CH;
- $Z^1$ is CH when the bond between atoms C5 and $Z^1$ is a single bond, and $Z^1$ is C when the bond between C5 and $Z^1$ is a double bond;
- $R^1$ is hydrogen or alkyl;
- $R^2$ is alkyl, hydroxyalkyl, optionally-substituted aralkyl, optionally-substituted cycloalkyl, heteroalkyl, optionally-substituted heterocyclyl, optionally-substituted aryl, or optionally-substituted heteroaryl;
- A is absent or —O—, —S(O)$_n$—, —CHR'—, —C(=O)—, or —NR$^3$—, wherein n is 0, 1, or 2, R' is hydrogen or alkyl, and R$^3$ is hydrogen, alkyl, optionally-substituted aryl, optionally-substituted heteroaryl, or optionally-substituted cycloalkyl;
- the bond between atoms C5 and $Z^1$ is a single or double bond; the bond between atoms C8 and C9 is a single or double bond; and;
- Y is an alkyl, heteroalkyl, optionally-substituted cycloalkyl, optionally-substituted aryl, or optionally substituted heteroaryl; or a pharmaceutically acceptable salt or ester thereof.

2. A compound according to claim 1, wherein $Z^1$ is —C— and the bond between $Z^1$ and C5 is a double bond.

3. A compound according to claim 1, wherein A is absent or —O—.

4. A compound according to claim 1, wherein $R^1$ is hydrogen.

5. A compound according to claim 1, wherein $R^2$ is selected from cyclopentyl, cyclohexyl, tetrahydropyranyl, piperidinyl, thianonyl, tetrahydro-1,1-dioxide-2-H-thiopyranyl, phenyl, and benzyl, wherein each of said $R^2$ groups is optionally-substituted with one of hydroxy, halogen, O(C$_{1-4}$alkyl), or S(O)$_2$(C$_{1-4}$alkyl); or $R^2$ is selected from C$_{1-4}$alkyl optionally substituted with one of hydroxy, O(C$_{1-4}$alkyl) or S(O)$_2$(C$_{1-4}$alkyl).

6. A compound according to claim 1, wherein Y is phenyl optionally substituted with halo, hydroxy, amino, alkyl or heteroaryl.

7. A compound having the formula Ia,

Ia wherein Y is aryl;
Z is CH;
A is absent or O;
$R^1$ is hydrogen;
$R^2$ is alkyl, hydroxyalkyl, optionally-substituted cycloalkyl, optionally-substituted heterocyclyl, optionally-substituted aryl, or optionally-substituted aralkyl; and the bond between C8 and C9 is a single or double bond.

8. A compound according to claim 1, having the formula

9. A pharmaceutical composition comprising a therapeutically effective amount of compound according to claim 1 in combination with a pharmaceutically acceptable carrier.

10. A method for treating a p38 mediated disorder, comprising administering to a patient in need of such treatment an effective amount of a compound according to claim 1, wherein the p38 mediated disorder is selected from the group consisting of arthritis, Crohn's disease, Alzheimer's disease, irritable bowel syndrome, adult respiratory distress syndrome, and chronic obstructive pulmonary disease.

* * * * *